United States Patent [19]

Benanti

[11] Patent Number: 4,797,423

[45] Date of Patent: Jan. 10, 1989

[54] LYSINE SALT OF 4-DIPHENYLACETIC ACID AND ITS OPHTHALMIC FOMULATIONS

[75] Inventor: Giuseppe Benanti, Santa'Agata Li Battiati, Italy

[73] Assignee: S.I.F.I. Societa Industria Farmaceutica Italiana S.p.A., Catania, Italy

[21] Appl. No.: 99,597

[22] Filed: Sep. 22, 1987

[30] Foreign Application Priority Data

Sep. 26, 1986 [IT] Italy ................. 21828 A/86

[51] Int. Cl.$^4$ ................. C07C 101/26; A61K 31/13
[52] U.S. Cl. ................. 514/914; 260/501.11; 514/555; 514/912
[58] Field of Search ........... 260/501.11; 514/555, 514/912, 914

[56] References Cited

U.S. PATENT DOCUMENTS

| | | | |
|---|---|---|---|
| 3,624,142 | 9/1964 | Shen et al. | 260/501.11 |
| 3,991,206 | 11/1976 | Tolman et al. | 514/568 |
| 4,189,499 | 2/1980 | Tosi et al. | 260/501.11 |
| 4,279,926 | 7/1981 | Brozzese et al. | 514/555 |
| 4,405,610 | 9/1983 | Krnjevic | 514/914 |
| 4,734,276 | 3/1988 | Ziegler | 260/501.11 |

FOREIGN PATENT DOCUMENTS

| | | | |
|---|---|---|---|
| 2205442 | 8/1973 | Fed. Rep. of Germany | 514/555 |
| 2419317 | 9/1975 | Fed. Rep. of Germany | 260/501.11 |
| 2711964 | 9/1978 | Fed. Rep. of Germany | 514/555 |

Primary Examiner—J. E. Evans
Attorney, Agent, or Firm—Oblon, Fisher, Spivak, McClelland & Maier

[57] ABSTRACT

It is hereby described and claimed the new lysine salt of 4-diphenylacetic acid, having an antiinflammatory and analgesic activity, its preparation method and the pharmaceutical compositions containing it which are therapeutically useful both systemically and topically.

1 Claim, No Drawings

LYSINE SALT OF 4-DIPHENYLACETIC ACID AND ITS OPHTHALMIC FOMULATIONS

DESCRIPTION

This invention refers to the lysine salt of 4-diphenylacetic acid, its preparation method and the pharmaceutical preparations containing it.

In particular, the object of the invention is the new lysine salt of 4-diphenylacetic acid (also named biphenylacetic acid) having the following formula:

which has a high antiinflammatory and analgesic activity and is used for the preparation of pharmaceutical formulations usable both systemically and topically as, for example, in ophthalmotherapy.

The aim of this invention is to have found a compound hydrosoluble soluble by salting out 4-diphenylacetic acid with lysine.

Further aim of this invention is of having unexpectedly found that the a.m. lysine salt, unlike other salts with analogous bases, such as arginine, presents a higher tolerability. Object of the invention is therefore of having found a new compound which amazingly shows a higher tolerability in comparison with analogous salts and the free acid itself and, furthermore, a better bioavailability. Another advantage of the lysine salt of 4-diphenylacetic acid consists in having the property of gradually and constantly releasing the active principle.

The mechanism of action of the lysine salt of 4-diphenylacetic acid is related to the block of the prostaglandins synthesis. "In vivo" the antiinflammatory activity of the product, orally administered in rats (test of the plantar edema from carrageenin and of arthritis from adjuvants), is considerably higher than the one of acetylsalicylic acid and phenylbutazone.

Moreover, lysine 4-diphenylacetate proved to be more effective than indomethacin, phenylbutazone and acetylsalicylic acid in reducing UV rays erythema in guinea pigs; this complies with the results "in vitro".

An "in vitro" experiment showed that lysine 4-diphenylacetate is a powerful inhibitor of the prostaglandins biosynthesis in presence of arachidonic acid added to lung omogenates of guinea pigs; this effect is higher than indomethacin. Furthermore, the lysine salt of 4-diphenylacetic acid is active as an analgesic for the pain caused by inflammation and as an antipyretic.

Thanks to its high activity and tolerability, the lysine salt of 4-diphenylacetic acid is profitably employed for the treatment of inflammations of various nature, both systemically and topically.

An important application of the product concerns the ophthalmic field.

It is well known that following a trauma, both mechanical and chemical, there is an immediate inflammatory reaction characterized by vasodilation, miosis, hyperemia and increase of the intraocular pressure due to alterations in the permeability of the aqueous/blood barrier. In these conditions, in the various ocular tissues, there is a remarkable increase in the biosynthesis of prostaglandins which are among the most powerful mediators of the inflammatory process. For such a pathology the administration of non-steroid antiinflammatory drugs inhibiting prostaglandins synthesis, is therefore indicated.

In the ophthalmic field, it is preferable to use topical preparations because the systemic administration of some drugs produces low concentrations in the ocular tissues and remarkable side effects.

For this purpose some non-steroid antiinflammatory drugs, known in literature, have been experimented and among these 4-diphenylacetic acid too (U.S. Pat. No. 3,991,206).

It is a product with a very low solubility in water and which is then used in form of oily suspension. This kind of formulation presents considerable disadvantages, in particular, the presence of crystals which make the compound badly tolerated from the ocular tissues. In fact, there is no evidence of a practical application of 4-diphenylacetic acid on the market of antiinflammatory agents for ophthalmic therapy.

The lysine salt of 4-diphenylacetic acid is prepared according to the acknowledged technique, making 4-diphenylacetic acid or one of its salts react with lysine in aqueous solution, at room temperature or slightly heating. The reaction may be performed with one of the stereoisomers L- or D-lysine or with the racemic form.

In order to explain the a.m. process, we report an example of the preparation of the lysine salt of 4-diphenylacetic acid.

EXAMPLE 2.12 g of 4-diphenylacetic acid (0.01 moles) are dissolved in 2N $NH_4OH$, the solution dried under vacuum and the product obtained (the ammonium salt of diphenylacetic acid) taken in the minimum quantity of water and added to an aqueous solution containing 1.46 g L-lysine base (0.01 moles). The solution is left at room temperature for some hours and then dried. The residue is crystallized from water/alcohol with a yield of 70%. The product obtained is a white crystalline solid, perfectly hydrosoluble, whose melting point is 225°–226° C. (with decomposition). The structure of the L-lysine salt of 4-diphenylacetic acid has been confirmed by NMR spectrum.

The same reaction was also carried out with D-lysine and D-L racemic form.

The pharmaceutical formulations are preferably those generally used for the preparation of systemic and topic drugs as, for example, tablets, suppositories, eye drops, creams, ointments, gel and other known formulations containing the lysine salt of 4-diphenylacetic acid.

The following examples describe some formulations containing the product and which have been used for the evaluation of the local tolerability and the capability of reducing the ocular inflammation caused by caustic agents with a consequent increase of prostaglandins levels in the aqueous humor.

FORMULATIONS BASED ON THE LYSINE SALT OF 4-DIPHENYLACETIC ACID

| Ointment (Formulation I) | |
|---|---|
| Lysine salt of 4-diphenylacetic acid equivalent to 4-diphenylacetic acid 3.00 g | 5.06 g |
| Liquid petrolatum | 20.00 g |
| Anhydrous lanolin | 5.00 g |
| White petrolatum | 69.94 g |
| Ointment (Formulation II) | |
| Lysine salt of 4-diphenylacetic acid equivalent to 4-diphenylacetic acid 3.00 g | 5.06 g |
| White wax | 4.00 g |

-continued

| | |
|---|---|
| Liquid petrolatum | 23.00 g |
| Dehymuls E | 6.70 g |
| Sterile distilled water q.s. to | 100.00 g |
| Cream (Formulation III) | |
| Lysine salt of 4-diphenylacetic acid equivalent to 4-diphenylacetic acid 3.00 g | 5.06 g |
| Polawax | 10.00 g |
| Robane | 4.00 g |
| Liquid petrolatum | 4.00 g |
| Sorbitol 70% | 5.00 g |
| Phenethyl alcohol | 0.25 g |
| Benzalkonium chloride | 0.02 g |
| Sterile distilled water q.s. to | 100.00 g |
| Gel (Formulation IV) | |
| Lysine salt of 4-diphenylacetic acid equivalent to 4-diphenylacetic acid 3.00 g | 5.06 g |
| Methylcellulose | 9.00 g |
| Phenethyl alcohol | 0.25 g |
| Benzalkonium chloride | 0.02 g |
| Sterile distilled water q.s. to | 100.00 g |
| Gel (Formulation V) | |
| Lysine salt of 4-diphenylacetic acid equivalent to 4-diphenylacetic acid 3.00 g | 5.06 g |
| Carbopol 940 | 1.50 g |
| Triethanolamine | 2.50 g |
| Phenethyl alcohol | 0.25 g |
| Benzalkonium chloride | 0.02 g |
| Sterile distilled water q.s. to | 100.00 g |
| Eye Drops (Formulation VI) | |
| Lysine salt of 4-diphenylacetic acid equivalent to 4-diphenylacetic acid 3.00 g | 5.0600 g |
| Hyaluronic acid | 0.4000 g |
| Sodium chloride | 0.3288 g |
| Benzalkonium chloride | 0.0200 g |
| Sterile distilled water q.s. to | 100.0000 ml |

(A)

EVALUATION OF THE LOCAL OCULAR TOLERABILITY

At first, the local tolerability of the preparations was evalued by applying them in the conjunctival sac of rabbits and repeating treatment according to the experimental scheme reported below.

EXPERIMENTAL CONDITIONS

Male albino rabbits, whose weight was between 1.8 and 2.5 Kg, were employed. The animals stayed in a conditioned environment and could freely reach water and feed. Before starting treatment the animals eyes were accurately controlled in order to verify the absence of ocular defects, conjunctival irritations or corneal lesions.

The liquid preparations were administered with a dosage of 0.2 ml/eye in the right conjunctival fornix. The solid preparations were administered with a dosage of 100 mg/eye in the right conjunctival fornix.

Six rabbits were employed for each of the a.m. preparations assayed.

After the application of the preparations under examination, the eyelids were accurately kept almost closed in order to avoid great losses of the solutions instilled and to promote the contact with the ocular tissues.

The treatment was: (a) repeated 6 times in succession every 60 minutes; (b) repeated 3 times a day every 6 hours (at 8 a.m., 2 p.m., 8 p.m.) for 21 days.

The left eye, which did not receive any treatment, was employed as a control.

The eyes were observed during treatment and one hour after the last treatment. Alterations of the conjuctiva were evalued employing the method described by Draize (Draize J. H., Dermal Toxicology, *Food-Drug Cosmet. Law J.* 10, 1955) according to the following values:

0=Normal. No reddening.

1=Hyperemia of some vessels, slight reddening.

2=Remarkably red coloured conjunctiva. The vessels cannot be singled out.

3=Intensely red coloured conjunctiva with marked vasal congestion.

The conditions of iris, cornea, the anterior portion of the eye and the ocular reflexes were evalued according to the method described by Baldwin H. A. et coll. (Baldwin H. A. et coll., *J. Soc. Cosmet. Chem.* 24, 181, 1973).

The results are reported in Tables 1 and 2 and show that all preparations examined proved to be well tolerated after acute treatment or administered for 21 days in the conjunctival fornix of the rabbit. There was no evidence of alterations involving other ocular tissues.

TABLE 1

Local tolerability of the formulations under examination, applied in the conjunctival fornix of the rabbit six times (every sixty minutes).

| | | Mean values assigned | |
|---|---|---|---|
| Treatment | Eye examined | Average | Incidence |
| Formulation I | R.E. | 1.00 | 4/6 |
| None | L.E. | 0.66 | 3/6 |
| Formulation II | R.E. | 1.16 | 5/6 |
| None | L.E. | 0.83 | 4/6 |
| Formulation III | R.E. | 0.66 | 3/6 |
| None | L.E. | 0.66 | 3/6 |
| Formulation IV | R.E. | 0.83 | 3/6 |
| None | L.E. | 0.83 | 2/6 |
| Formulation V | R.E. | 0.66 | 4/6 |
| None | L.E. | 0.33 | 3/6 |
| Formulation VI | R.E. | 0.66 | 4/6 |
| None | L.E. | 0.66 | 4/6 |
| Formulation VII | R.E. | 0.33 | 2/6 |
| None | L.E. | 0.66 | 2/6 |

The mean values were calculated summing up the individual values and dividing the result by the number of controls carried out.

TABLE 2

Local tolerability of the formulations under examination, applied in the conjunctival fornix of the rabbit three times a day for 21 days.

| | | Mean values assigned | |
|---|---|---|---|
| Treatment | Eye examined | Average | Incidence |
| Formulation I | R.E. | 1.66 | 5/6 |
| None | L.E. | 0.83 | 4/6 |
| Formulation II | R.E. | 0.83 | 3/6 |
| None | L.E. | 0.83 | 4/6 |
| Formulation III | R.E. | 1.33 | 5/6 |
| None | L.E. | 0.83 | 4/6 |
| Formulation IV | R.E. | 0.66 | 3/6 |
| None | L.E. | 0.66 | 2/6 |
| Formulation V | R.E. | 0.83 | 4/6 |
| None | L.E. | 0.33 | 2/6 |
| Formulation VI | R.E. | 0.66 | 2/6 |
| None | L.E. | 0.66 | 2/6 |
| Formulation VII | R.E. | 0.66 | 3/6 |
| None | L.E. | 0.33 | 2/6 |

The mean values were calculated summing up the individual values and dividing the result by the number of controls carried out.

(B)

EVALUATION OF THE OCULAR ANTIINFLAMMATORY ACTIVITY AFTER TOPICAL APPLICATION

EXPERIMENTAL CONDITIONS

Male New Zealand rabbits, whose weight was between 1.8 and 2.5 Kg, were employed. Th animals stayed in a conditioned environment and could freely reach water and feed.

Before starting treatment, the eyes were accurately controlled in order to verify the absence of ocular defects, conjunctival irritations or corneal lesions.

An experimental inflammation of the ocular tissues was induced in rabbits, instilling one drop 0.5N sodium hydroxide solution and one drop of absolute ethanol in the right eye. After thirty minutes, following an accurate examination of the ocular tissues, the treatment with the a.m. preparation started. Different groups of animals were treated with the formulations lacking of the active principle (lysine salt of 4-diphenylacetic acid).

Each group was made up of 4 animals.

The liquid and solid preparations were administered with a dosage of 0.2 ml/eye and 100 mg/eye, respectively.

Alterations of the conjunctiva, iris and cornea were evaluated according to the method described by Draize J. H. immediately before starting treatment with the formulations under examination and then after 1, 2, 3, 5, 7 and 12 days of treatment.

The following parameters were adopted:
A. Conjunctival congestion
0=Normal
1=Hyperemia of some vessels with slight reddening.
2=Remarkably red coloured conjunctiva. The vessels cannot be singled out.
3=Intensely red coloured conjunctiva.
B. Conjunctival edema
0=Normal
1=Considerable swelling without eyelid eversion
2=Swelling with slight eversion of the superior eyelid.
3=Swelling of both eyelids with eversion.
4=Swelling of both eyelids, particularly marked in the superior eyelid.
C. Presence of discharge material
0=Normal, absent material
1=Discharge material in the internal portion of the eye.
2=Abundant discharge material, easy to observe, located on the eyelids and the surrounding hair.
3=Abundant discharge material spreading externally and wetting the periorbital area.
D. Iris inflammation
0=Normal.
1=Slight hyperemia of the secondary vessels.
2=Slight hyperemia of the tertiary vessels; modest hyperemia of the secondary vessels.
3=Modest hyperemia of the secondary and tertiary vessels; slight stromal swelling.
4=Remarkable hyperemia of the secondary and tertiary vessels with marked stromal swelling.
E. Corneal inflammation
0=Normal cornea.
1=Slight loss of transparence in the anterior half of the stroma. Iris details are visible.
2=Modest loss of transparence extending to the endothelium. Iris details appear a bit obscured.
3=Involvement of the whole stroma with necrotic areas. Iris details are not visible.
4=Total opacity.

The values were assigned following a blind procedure.

The evaluation of the differences between the group of animals treated only with the vehicle of the formulations, was performed by means of the variance analysis according to the common statistical tests (Finney D. J., Statistical mthods in biological assay, Hafner Publishing Co. N.Y. 1964).

The signs of experimentally induced inflammation consist in conjunctival hyperemia, conjunctival chemosis and a slight turbidness of the aqueous humor.

The inflammation develops regularly and its duration is constant.

As widely reported in Tables 3 to 16, the formulations examined proved to be effective, as antiinflammatory agents, rapidly improving the ocular inflammtion within 3 days from the beginning of treatment and achieving a complete recovery within 6-7 days.

On the contrary, the animals treated only with the vehicle of the formulations under examination showed a clear difference achieving improvement of the inflammation within 6-7 days and complete recovery within the 12th day.

The statistical analyses carried out by comparing treated with control groups confirm what stated above.

The comparison between treated groups and controls (variability among drugs) is significantly different from 0 (p 0.05) the difference of the two time curves is significant too (p 0.05).

The results show that the formulations proved to be well tolerated and have a high antiinflammatory activity.

TABLE 3

Alterations of the ocular tissues after administration of an inflammatory agent and consequent treatment with FORMULATION I.

| Days of treatment | Mean values assigned | | | | |
|---|---|---|---|---|---|
| | Conjunctival congestion | Conjunctival edema | Discharge material | Iris inflam. | Corneal inflam. |
| 0 | 3.00 | 3.75 | 2.50 | 2.75 | 3.00 |
| 1 | 3.00 | 3.75 | 2.25 | 2.50 | 2.75 |
| 2 | 2.00 | 2.25 | 1.00 | 1.50 | 1.75 |
| 3 | 1.25 | 1.00 | 1.00 | 1.25 | 1.75 |
| 5 | 0.50 | 0.50 | 0.50 | 0.50 | 0.75 |
| 7 | 0.50 | 0.25 | 0.25 | 0.50 | 0.50 |
| 12 | 0.00 | 0.00 | 0.25 | 0.25 | 0.00 |

The mean values were calculated summing up the individual values and dividing the result by the number of controls carried out.

TABLE 4

Alterations of the ocular tissues after administration of an inflammatory agent and consequent treatment with the VEHICLE OF FORMULATION I.

| Days of treatment | Mean values assigned | | | | |
|---|---|---|---|---|---|
| | Conjunctival congestion | Conjunctival edema | Discharge material | Iris inflam. | Corneal inflam. |
| 0 | 3.00 | 3.75 | 2.50 | 2.75 | 3.00 |
| 1 | 3.00 | 3.50 | 2.50 | 2.50 | 2.75 |
| 2 | 3.00 | 3.50 | 2.25 | 2.50 | 2.50 |
| 3 | 2.50 | 3.00 | 2.00 | 2.00 | 2.00 |
| 5 | 2.00 | 2.50 | 1.00 | 1.25 | 1.00 |
| 7 | 1.50 | 2.00 | 1.00 | 0.75 | 0.50 |

TABLE 4-continued

Alterations of the ocular tissues after administration of an inflammatory agent and consequent treatment with the VEHICLE OF FORMULATION I.

| Days of treatment | Mean values assigned | | | | |
|---|---|---|---|---|---|
| | Conjunctival congestion | Conjunctival edema | Discharge material | Iris inflam. | Corneal inflam. |
| 12 | 1.50 | 1.00 | 1.00 | 0.50 | 0.50 |

The mean values were calculated summing up the individual values and dividing the result by the number of controls carried out.

TABLE 5

Alterations of the ocular tissues after administration of an inflammatory agent and consequent treatment with FORMULATION II.

| Days of treatment | Mean values assigned | | | | |
|---|---|---|---|---|---|
| | Conjunctival congestion | Conjunctival edema | Discharge material | Iris inflam. | Corneal inflam. |
| 0 | 3.00 | 3.50 | 2.25 | 2.75 | 2.75 |
| 1 | 3.00 | 3.50 | 2.25 | 2.50 | 2.75 |
| 2 | 2.00 | 1.75 | 1.00 | 1.50 | 2.00 |
| 3 | 2.00 | 1.50 | 1.00 | 1.00 | 1.00 |
| 5 | 0.75 | 0.75 | 0.50 | 0.50 | 0.75 |
| 7 | 0.25 | 0.00 | 0.25 | 0.50 | 0.25 |
| 12 | 0.00 | 0.00 | 0.00 | 0.00 | 0.00 |

The mean values were calculated summing up the individual values and dividing the result by the number of controls carried out.

TABLE 6

Alterations of the ocular tissues after administration of an inflammatory agent and consequent treatment with VEHICLE OF FORMULATION II.

| Days of treatment | Mean values assigned | | | | |
|---|---|---|---|---|---|
| | Conjunctival congestion | Conjunctival edema | Discharge material | Iris inflam. | Corneal inflam. |
| 0 | 3.00 | 3.50 | 2.25 | 2.00 | 3.00 |
| 1 | 3.00 | 3.50 | 2.00 | 2.00 | 3.00 |
| 2 | 3.00 | 3.00 | 2.00 | 1.75 | 2.50 |
| 3 | 3.00 | 2.75 | 2.00 | 1.50 | 2.00 |
| 5 | 2.50 | 2.25 | 1.50 | 1.00 | 1.00 |
| 7 | 2.00 | 2.00 | 1.25 | 0.75 | 0.75 |
| 12 | 0.75 | 1.00 | 0.50 | 0.00 | 0.50 |

The mean values were calculated summing up the individual values and dividing the result by the number of controls carried out.

TABLE 7

Alterations of the ocular tissues after administration of an inflammatory agent and consequent treatment with FORMULATION III.

| Days of treatment | Mean values assigned | | | | |
|---|---|---|---|---|---|
| | Conjunctival congestion | Conjunctival edema | Discharge material | Iris inflam. | Corneal inflam. |
| 0 | 3.00 | 4.00 | 2.50 | 2.50 | 3.25 |
| 1 | 2.75 | 3.75 | 2.50 | 2.00 | 3.00 |
| 2 | 2.00 | 3.00 | 1.75 | 1.50 | 2.75 |
| 3 | 2.00 | 2.50 | 1.75 | 1.50 | 2.50 |
| 5 | 1.00 | 1.00 | 0.75 | 0.50 | 1.50 |
| 7 | 0.75 | 0.50 | 0.25 | 0.00 | 0.50 |
| 12 | 0.00 | 0.00 | 0.00 | 0.00 | 0.00 |

The mean values were calculated summing up the individual values and dividing the result by the number of controls carried out.

TABLE 8

Alterations of the ocular tissues after administration of an inflammatory agent and consequent treatment with the VEHICLE OF FORMULATION III.

| Days of treatment | Mean values assigned | | | | |
|---|---|---|---|---|---|
| | Conjunctival congestion | Conjunctival edema | Discharge material | Iris inflam. | Corneal inflam. |
| 0 | 3.00 | 3.50 | 2.50 | 2.00 | 2.50 |
| 1 | 3.00 | 3.25 | 2.50 | 2.00 | 2.50 |
| 2 | 3.00 | 3.25 | 2.50 | 1.50 | 2.00 |
| 3 | 2.50 | 2.25 | 2.00 | 1.25 | 1.25 |
| 5 | 2.50 | 2.00 | 2.00 | 1.00 | 1.00 |
| 7 | 1.75 | 1.50 | 1.25 | 1.00 | 0.75 |
| 12 | 0.75 | 0.50 | 0.75 | 0.00 | 0.25 |

The mean values were calculated summing up the individual values and dividing the result by the number of controls carried out.

TABLE 9

Alterations of the ocular tissues after administration of an inflammatory agent and consequent treatment with FORMULATION IV.

| Days of treatment | Mean values assigned | | | | |
|---|---|---|---|---|---|
| | Conjunctival congestion | Conjunctival edema | Discharge material | Iris inflam. | Corneal inflam. |
| 0 | 3.00 | 3.25 | 3.00 | 2.25 | 3.00 |
| 1 | 3.00 | 3.00 | 2.75 | 2.25 | 3.00 |
| 2 | 2.25 | 2.00 | 2.00 | 2.00 | 2.00 |
| 3 | 1.75 | 1.50 | 1.00 | 1.25 | 1.75 |
| 5 | 1.00 | 1.00 | 0.75 | 0.75 | 1.00 |
| 7 | 0.25 | 0.50 | 0.25 | 0.00 | 0.50 |
| 12 | 0.00 | 0.00 | 0.00 | 0.00 | 0.00 |

The mean values were calculated summing up the individual values and dividing the result by the number of controls carried out.

TABLE 10

Alterations of the ocular tissues after administration of an inflammatory agent and consequent treatment with the VEHICLE OF FORMULATION IV.

| Days of treatment | Mean values assigned | | | | |
|---|---|---|---|---|---|
| | Conjunctival congestion | Conjunctival edema | Discharge material | Iris inflam. | Corneal inflam. |
| 0 | 2.75 | 3.25 | 2.50 | 2.50 | 2.75 |
| 1 | 2.75 | 3.25 | 2.25 | 2.00 | 2.25 |
| 2 | 2.50 | 3.00 | 2.00 | 2.00 | 2.25 |
| 3 | 2.50 | 2.25 | 1.75 | 1.50 | 2.00 |
| 5 | 2.25 | 1.75 | 1.50 | 1.00 | 1.25 |
| 7 | 1.50 | 0.75 | 1.00 | 0.50 | 0.50 |
| 12 | 0.75 | 0.50 | 0.50 | 0.00 | 0.00 |

The mean values were calculated summing up the individual values and dividing the result by the number of controls carried out.

TABLE 11

Alterations of the ocular tissues after administration of an inflammatory agent and consequent treatment with FORMULATION V.

| Days of treatment | Mean values assigned | | | | |
|---|---|---|---|---|---|
| | Conjunctival congestion | Conjunctival edema | Discharge material | Iris inflam. | Corneal inflam. |
| 0 | 3.00 | 3.50 | 2.75 | 1.75 | 2.75 |
| 1 | 2.75 | 3.00 | 2.50 | 1.50 | 2.75 |
| 2 | 2.00 | 2.25 | 2.00 | 1.25 | 2.00 |
| 3 | 1.25 | 1.00 | 1.25 | 0.75 | 1.00 |
| 5 | 0.50 | 0.50 | 0.25 | 0.25 | 0.50 |
| 7 | 0.25 | 0.00 | 0.00 | 0.00 | 0.00 |
| 12 | 0.00 | 0.00 | 0.00 | 0.00 | 0.00 |

The mean values were calculated summing up the individual values and dividing the result by the number of controls carried out.

TABLE 12

Alterations of the ocular tissues after administration of an inflammatory agent and consequent treatment with the VEHICLE OF FORMULATION V.

| Days of treatment | Mean values assigned | | | | |
|---|---|---|---|---|---|
| | Conjunctival congestion | Conjunctival edema | Discharge material | Iris inflam. | Corneal inflam. |
| 0 | 3.00 | 2.75 | 2.50 | 2.25 | 2.50 |
| 1 | 3.00 | 2.75 | 2.50 | 2.25 | 2.50 |
| 2 | 2.75 | 2.50 | 2.50 | 1.75 | 1.75 |
| 3 | 2.75 | 2.00 | 2.25 | 1.50 | 1.75 |
| 5 | 2.50 | 1.75 | 2.00 | 1.00 | 1.25 |
| 7 | 1.00 | 1.25 | 1.00 | 0.50 | 0.75 |
| 12 | 1.00 | 0.75 | 0.50 | 0.00 | 0.50 |

The mean values were calculated summing up the individual values and dividing the result by the number of controls carried out.

TABLE 13

Alterations of the ocular tissues after administration of an inflammatory agent and consequent treatment with FORMULATION VI.

| Days of treatment | Mean values assigned | | | | |
|---|---|---|---|---|---|
| | Conjunctival congestion | Conjunctival edema | Discharge material | Iris inflam. | Corneal inflam. |
| 0 | 2.75 | 3.25 | 2.50 | 2.25 | 2.50 |
| 1 | 2.75 | 3.00 | 2.25 | 1.75 | 2.50 |
| 2 | 2.00 | 2.25 | 1.75 | 1.50 | 2.25 |
| 3 | 1.50 | 1.25 | 1.00 | 1.00 | 1.50 |
| 5 | 1.00 | 0.75 | 0.50 | 0.25 | 0.50 |
| 7 | 0.25 | 0.25 | 0.00 | 0.00 | 0.00 |
| 12 | 0.00 | 0.00 | 0.00 | 0.00 | 0.00 |

The mean values were calculated summing up the individual values and dividing the result by the number of controls carried out.

TABLE 14

Alterations of the ocular tissues after administration of an inflammatory agent and consequent treatment with the VEHICLE OF FORMULATION VI.

| Days of treatment | Mean values assigned | | | | |
|---|---|---|---|---|---|
| | Conjunctival congestion | Conjunctival edema | Discharge material | Iris inflam. | Corneal inflam. |
| 0 | 3.00 | 4.00 | 3.00 | 2.75 | 2.50 |
| 1 | 3.00 | 4.00 | 3.00 | 2.50 | 2.50 |
| 2 | 3.00 | 3.50 | 2.75 | 2.25 | 2.00 |
| 3 | 3.00 | 3.50 | 2.75 | 2.25 | 2.00 |
| 5 | 2.25 | 2.00 | 2.00 | 1.50 | 1.25 |
| 7 | 1.75 | 1.75 | 1.50 | 1.00 | 1.00 |
| 12 | 0.50 | 0.75 | 0.50 | 0.00 | 0.50 |

The mean values were calculated summing up the individual values and dividing the result by the number of controls carried out.

TABLE 15

Alterations of the ocular tissues after administration of an inflammatory agent and consequent treatment with FORMULATION VII.

| Days of treatment | Mean values assigned | | | | |
|---|---|---|---|---|---|
| | Conjunctival congestion | Conjunctival edema | Discharge material | Iris inflam. | Corneal inflam. |
| 0 | 3.00 | 4.00 | 3.00 | 3.00 | 2.75 |
| 1 | 2.50 | 3.75 | 2.50 | 2.75 | 2.75 |
| 2 | 2.00 | 2.25 | 2.00 | 2.25 | 2.50 |
| 3 | 1.25 | 1.75 | 1.25 | 1.25 | 1.00 |
| 5 | 0.50 | 0.75 | 0.50 | 0.75 | 0.50 |
| 7 | 0.25 | 0.25 | 0.50 | 0.25 | 0.00 |
| 12 | 0.00 | 0.25 | 0.00 | 0.00 | 0.00 |

The mean values were calculated summing up the individual values and dividing the result by the number of controls carried out.

TABLE 16

Alterations of the ocular tissues after administration of an inflammatory agent and consequent treatment with the VEHICLE OF FORMULATION VII.

| Days of treatment | Mean values assigned | | | | |
|---|---|---|---|---|---|
| | Conjunctival congestion | Conjunctival edema | Discharge material | Iris inflam. | Corneal inflam. |
| 0 | 3.00 | 3.50 | 3.00 | 2.75 | 2.25 |
| 1 | 3.00 | 3.50 | 2.50 | 2.75 | 2.25 |
| 2 | 3.00 | 3.50 | 2.00 | 2.00 | 2.00 |
| 3 | 3.00 | 3.25 | 1.75 | 2.00 | 2.00 |
| 5 | 2.00 | 2.25 | 1.25 | 1.25 | 1.00 |
| 7 | 1.50 | 1.00 | 1.00 | 1.00 | 0.50 |
| 12 | 0.75 | 0.50 | 0.00 | 0.25 | 0.00 |

The mean values were calculated summing up the individual values and dividing the result by the number of controls carried out.

I claim:

1. An ophthalmic therapeutic composition, comprising:
a therapeutically effective amount of the lysine salt of 4-diphenylacetic acid of the formula:

$$\text{(C}_6\text{H}_5\text{)-(C}_6\text{H}_4\text{)}-CH_2-COOH \cdot NH_2-(CH_2)_4-\underset{NH_2}{CH}-COOH$$

in combination with pharmaceutically acceptable excipients.

* * * * *